(12) United States Patent
Vogt et al.

(10) Patent No.: US 9,480,778 B2
(45) Date of Patent: *Nov. 1, 2016

(54) COATING METHOD AND COATING DEVICE

(75) Inventors: Sebastian Vogt, Erfurt (DE);
Klaus-Dieter Kühn,
Marburg-Elnhausen (DE)

(73) Assignee: Heraeus Medical GmbH, Wehrheim (DE)

( * ) Notice: Subject to any disclaimer, the term of this patent is extended or adjusted under 35 U.S.C. 154(b) by 486 days.

This patent is subject to a terminal disclaimer.

(21) Appl. No.: 13/333,009

(22) Filed: Dec. 21, 2011

(65) Prior Publication Data

US 2012/0164312 A1    Jun. 28, 2012

Related U.S. Application Data

(60) Provisional application No. 61/432,798, filed on Jan. 14, 2011.

(30) Foreign Application Priority Data

Dec. 23, 2010   (DE) .......................... 10 2010 055 560

(51) Int. Cl.
*A61L 27/54*       (2006.01)
*B05D 1/18*        (2006.01)

(52) U.S. Cl.
CPC .......... *A61L 27/54* (2013.01); *A61L 2300/406* (2013.01); *A61L 2420/02* (2013.01); *B05D 1/18* (2013.01); *B05D 2451/00* (2013.01)

(58) Field of Classification Search
USPC ......................................... 132/73.5; 427/2.26
See application file for complete search history.

(56) References Cited

U.S. PATENT DOCUMENTS

| 2,268,642 | A | * | 1/1942 | Carter ........................... 510/118 |
| 4,282,891 | A | * | 8/1981 | Duceppe ...................... 132/73.5 |
| 5,607,685 | A | | 3/1997 | Cimbollek et al. |
| 5,679,646 | A | | 10/1997 | Cimbollek et al. |
| 6,451,373 | B1 | | 9/2002 | Hossainy et al. |
| 6,984,410 | B2 | | 1/2006 | Vogt et al. |
| 7,030,093 | B2 | | 4/2006 | Vogt et al. |

(Continued)

FOREIGN PATENT DOCUMENTS

DE      4404018 A1     8/1995
DE     10142465 A1     7/2003

(Continued)

OTHER PUBLICATIONS

Office Action issued Jun. 25, 2013 in CA Application No. 2,760,908.
English translation of Office Action issued Oct. 29, 2013 in CN Application No. 201110439669.7.

(Continued)

*Primary Examiner* — Dah-Wei D Yuan
*Assistant Examiner* — Andrew Bowman
(74) *Attorney, Agent, or Firm* — Panitch Schwarze Belisario & Nadel LLP

(57) ABSTRACT

A method for coating at least regions of a medical implant includes providing a medical implant having a surface to be coated, and immersing the surface of the medical implant into a liquid including at least one pharmaceutically active substance, whereby the liquid is transferred to the surface of the medical implant due to the immersing. The method also includes pulling the surface of the medical implant out of the liquid, whereby part of the liquid remains adhering to the surface of the medical implant.

6 Claims, 2 Drawing Sheets

(56) References Cited

U.S. PATENT DOCUMENTS

| | | |
|---|---|---|
| 7,563,324 B1 | 7/2009 | Chen et al. |
| 8,973,521 B2 * | 3/2015 | Vogt .................. A61L 27/54 118/264 |
| 9,078,959 B2 * | 7/2015 | Vogt .................. A61L 27/306 |
| 2003/0078242 A1 | 4/2003 | Raad et al. |
| 2003/0229401 A1 | 12/2003 | Mansouri et al. |
| 2005/0031664 A1 | 2/2005 | Vogt et al. |
| 2005/0170070 A1 | 8/2005 | Layrolle et al. |
| 2006/0029722 A1 | 2/2006 | Larson et al. |
| 2006/0251824 A1 | 11/2006 | Boulais et al. |
| 2007/0125247 A1 | 6/2007 | Kunstmann et al. |
| 2007/0281072 A1 | 12/2007 | O'Connor et al. |
| 2008/0206442 A1 | 8/2008 | Shekalim et al. |

FOREIGN PATENT DOCUMENTS

| | | |
|---|---|---|
| DE | 10351150 A1 | 5/2005 |
| EP | 0623349 A1 | 11/1994 |
| EP | 1374923 A2 | 1/2004 |
| EP | 1470829 A1 | 10/2004 |
| WO | 2005037447 A1 | 4/2005 |
| ZA | 200206983 A | 5/2003 |

OTHER PUBLICATIONS

Office Action issued Jul. 5, 2011 in DE Application No. 10 2010 055 560.6.

European Search Report issued Sep. 15, 2014 in EP Application No. 11009385.3.

\* cited by examiner

COATING METHOD AND COATING DEVICE

CROSS-REFERENCE TO RELATED APPLICATIONS

The present application claims priority to U.S. Provisional Patent Application No. 61/432,798, entitled "Coating Process and Coating Apparatus" and filed Jan. 14, 2011.

BACKGROUND OF THE INVENTION

The present invention relates generally to a method for coating, at least regions of, a medical implant, preferably of an artificial joint or a fixation for a joint.

The present invention also relates generally to a device for coating, at least regions of, a medical implant using the method.

The coating of medical implants with pharmaceutical agents has garnered increasing attention in recent years. Antibiotic protection of the surface of implant materials is a central application of coating methods in this context. The improvement of the surface compatibility of medical implants that non-cemented medical implants in order to improve osseointegration is another important application.

Any implantation of articular endoprostheses, and of osteosynthesis materials as well, is associated with a certain risk of microbial contamination. Successful colonisation of microbial pathogens on the surface of the implant can lead to the manifestation of post-operative osteitis/osteomyelitis. Osteitis/osteomyelitis is a severe complication for the patient and, in addition, associated with substantial costs.

Gentamicin-doped PMMA bone cement has been in clinical use with cemented articular endoprostheses for decades with much success. The broadband antibiotic, gentamicin, contained in the bone cement protects the surface of the bone cement effectively from bacterial infections.

With regard to non-cemented articular endoprostheses and osteosynthesis materials, a number of approaches has been proposed in order to also attain local antibiotic protection of the implant surfaces.

For example, the use of poorly water-soluble antibiotic salts has been described in several patent documents. For exemplary purposes, EP 0 623 349 A1, EP 1 470 829 A1, EP 1 374 923 A2, DE 101 42 465 A1, and DE 44 04 018 A1 can be cited in this context. The poorly water-soluble salts dissolve while releasing the antibiotics contained therein as a result of the action of body fluids. Prolonged release of the agent is advantageous. However, the laborious production of the salts is disadvantageous.

Alternatively, it is feasible to use water-soluble antibiotic salts. This is associated with a problem related to fixation of the antibiotic on the implant surface.

The majority of coatings that have been described thus far is preferably intended for the manufacture of coated implants under industrial conditions. This means that the industrial coating of the implants can only involve few agents that are relevant for large-scale use in order to be able to guarantee that the industrial manufacture is economic through sufficiently large throughput.

In particular in the case of antibiotic coatings, though, considering the increasingly problematic resistance status and the ensuing increased manifestation of multi-resistant pathogens, such as MRSA and MRSE, it is of interest to use antibiotics or combinations of antibiotics, which are specifically adapted to the germ at hand, for the coating of revision prostheses in one-stage or two-stage septic articular endoprosthesis replacement in order to ensure effective initial antibiotic protection of the implant surfaces.

This is disadvantageous in that the methods for coating the medical implants are relatively laborious. Variable short-term application is not feasible. Various scenarios then necessitate the stock-keeping of various coated medical implants in order to meet the needs of the different patients. This requires extensive stock-keeping and prevents uncommon mixtures for specific cases.

BRIEF SUMMARY OF THE INVENTION

Accordingly, it is an objective of a preferred embodiment of the present invention to overcome the disadvantages of the prior art. In particular, a simple and easy-to-use method and a device are to be provided for this purpose that can be used to coat a medical prosthesis without interfering with an ongoing surgery (OR). The aim is to be able to coat as many different medical implants as possible using the same method and the same device. Moreover, the method and the device should be variable to use such that they can be adapted to the medical needs, in particular to a suitable medication for the patient. The cleanliness required in operating theatres is another factor to take into account.

It is also an objective of a preferred embodiment of the present invention to develop a coating method that is as simple as possible and can be used by the OR staff during an ongoing surgery, with the least time expenditure, to coat very different implants from any manufacturers with pharmaceutical preparations. Moreover, it is an object of a preferred embodiment of the present invention to develop a simple coating device that allows the OR staff to coat implants under OR conditions with the least effort possible. Moreover, the device is to be designed such that, to the extent possible, no excess material from the production of the coating can contaminate the OR area. Another object is that the device should, in particular, be suitable for the coating of non-cemented articular endoprostheses and osteosynthesis materials.

An object of a preferred embodiment of the present invention is met in that a medical implant having a surface to be coated is provided, the medical implant surface to be coated is immersed into a liquid comprising at least one pharmaceutically active substance, whereby liquid is transferred to the surface of the medical implant owing to the immersing, and the medical implant surface to be coated is pulled out of the liquid, whereby part of the liquid remains adhering to the medical implant surface to be coated.

Methods according to a preferred embodiment of the present invention are carried out before inserting the medical implants. Accordingly, the methods proceed "ex vivo."

According to a preferred embodiment of the present invention, a pharmaceutically active substance shall be understood to mean pharmaceutically effective means or means with a pharmacological effect as well as means that support a pharmacological effect or support in any other way the self-healing forces of the body. Examples include antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

According to a preferred embodiment of the present invention, immersing is to be understood to not only mean immersing in a large quantity of liquid. Provided the shape of the liquid container matches the shape of the medical implant to be coated, even a small quantity of liquid can be sufficient for coating the entire medical implant surface to be coated. The liquid is then pushed upward between the medical implant and the liquid container.

The scope of a preferred embodiment of the present invention also includes that the implant to be coated is introduced into and pulled out of the liquid repeatedly, if applicable.

Moreover, a preferred embodiment of the present invention can provide the medical implant to be coated to be selected from hip endoprostheses, shoulder endoprostheses, elbow endoprostheses, marrow nails, and osteosynthesis plates.

The scope of a preferred embodiment of the present invention can also provide that the liquid comprises an aqueous solution of an antibiotic, preferably that an aqueous gentamicin sulfate solution with a gentamicin sulfate content of 10.0 to 88.0% by weight is used, whereby it is particularly preferred to use a gentamicin sulfate solution with a gentamicin sulfate content of 75.0 to 80.0% by weight. The gentamicin sulfate solution has an oily-viscous consistency and adheres very well to metal surfaces.

In this context, a preferred embodiment of the present invention can further provide that common pharmaceutical stabilisers are contained in the gentamicin sulfate solutions. These improve the durability and thus the usability of the liquid to be applied.

A preferred embodiment of the present invention can also provide for the use of other aminoglycoside antibiotic solutions such as aqueous solutions of tobramicin sulfate, amikacin sulfate, netilmicin sulfate, and sisomicin sulfate as liquid or components of the liquid. It is also feasible to use aqueous solutions of vancomycin, dalbavancin, ramoplanin, daptomycin, moxifloxacin, clindamycin, and lincomycin.

Moreover, the scope of a preferred embodiment of the present invention can provide for the use of combinations of solutions of different antibiotics as liquid. Examples include two-antibiotic combinations of gentamicin sulfate and vancomycin hydrochloride, the two-antibiotic combination of daptomycin and gentamicin sulfate, and the two-antibiotic combination of gentamicin sulfate and clindamycin as well as the three-antibiotic combination of gentamicin sulfate and vancomycin hydrochloride and clindamycin hydrochloride.

A preferred embodiment of the present invention can further provide for antiseptics solutions to be used as liquid, in particular solutions of chlorohexidine digluconate, octenidine dihydrochloride, and polyhexanide.

According to a particularly advantageous refinement, a preferred embodiment of the present invention can provide the liquid to be provided in a container having an opening, whereby the medical implant is introduced through the opening in order to coat the surface to be coated.

Methods according to a preferred embodiment of the present invention can also be characterised in that the medical implant is pushed through a membrane or a membrane is opened before immersing the medical implant in the liquid, whereby the membrane covers at least regions of the liquid, preferably the membrane covers all of the liquid in the container. Owing to these two measures, the method is easy to use at different sites, since the device to be used is easy to transport.

Another refinement, according to a preferred embodiment of the present invention, of the method can provide a liquid matching the treatment scenario to be provided.

A preferred embodiment of the present invention can also provide that an antibiotic or mixture of antibiotics matching the treatment scenario is introduced into the liquid. These two measures allow for individual adaptation to the actual treatment scenario of the respective patient.

In this context, a preferred embodiment of the present invention can provide the medical implant to be introduced into a container, in which the liquid is situated, before immersing it into the liquid, and to be pulled out of the container after transfer of the liquid to the medical implant.

A preferred embodiment of the present invention can also provide that the medical implant is pushed through a membrane or a membrane is opened before immersing the medical implant in the liquid, whereby the membrane covers at least regions of the liquid, preferably the membrane covers all of the liquid in the container. The membrane prevents contamination of the liquid prior to its use. Puncturing the membrane ensures that the protective membrane is opened only shortly before its use. For this purpose, the structure of the membrane should be such that no shreds or other parts of the membrane can enter into the liquid or adhere to the medical implant.

It is particularly preferred for part of the transferred liquid to be wiped off, in particular upon pulling the medical implant out of the container, preferably at a wiper designed for this purpose. This can prevent or at least reduce contamination of the surroundings, for example, in particular of an OR area, by the liquid. This is advisable especially upon the use of antibiotics since it allows the development of resistant pathogens in the OR area to be prevented.

Moreover, a preferred embodiment of the present invention can provide that at least 50% of the surface of the medical implant, preferably at least 80%, particularly preferably at least 90% of the surface of the medical implant, are being coated.

Methods according to a preferred embodiment of the present invention can also be characterised in that a second liquid, preferably comprising at least one pharmaceutically active substance, is transferred through a transfer means to the surface of the medical implant before immersing the medical implant.

In this context, a preferred embodiment of the present invention can provide for the medical implant to be swept over an transfer means that can be deformed elastically, whereby the second liquid is transferred from the transfer means to the medical implant surface to be coated while sweeping over the transfer means. What using an transfer means that can be deformed elastically achieves is that the second liquid applied by the transfer means can also be applied onto an irregularly shaped medical implant in a widespread manner. It is particularly preferred for the transfer means to also be porous, whereby the second liquid is stored in the pores of the transfer means. The transfer means can then be arranged above the (first) liquid without the second liquid dripping into the (first) liquid. This is advantageous, in particular in combination with a membrane for covering the (first) liquid.

A preferred embodiment of the present invention can also provide that a powder is applied to the wetted surface of the medical implant after transfer of the liquid to the medical implant, preferably in that the medical implant is immersed into a powder, whereby the powder preferably comprises at least one bone growth-promoting substance.

In order to render the coated region and the completeness of coating visible, the invention can provide that the liquid is made to be coloured such that the coated region of the medical implant can be identified by colour.

In this context, a preferred embodiment of the present invention can provide that the completeness of coating of the region to be coated is tested by means of the colouration.

A preferred embodiment of the present invention can also provide for the method to be repeated as often as required for complete coating of the medical implant surface to be coated to be attained. In particular in the context of colouration of the liquid and testing of the completeness of coating through the colouration, this is advantageous according to the invention in order to generate a sufficiently coated medical implant.

It can be advantageous for the container with the implant introduced into it to be closed and/or sealed. This can be done through closing a lid that is designed for this purpose.

A preferred embodiment of the present invention can provide the container with the implant enclosed therein to be shaken briefly subsequently.

The object of a preferred embodiment of the present invention is also met by a device for coating, at least regions of, a medical implant using the method, whereby the device comprises a container that has a liquid that contains at least one pharmaceutically active substance, and the container comprises an opening for introducing and pulling out the medical implant.

In this context, a preferred embodiment of the present invention can provide the opening to be closed through a pull-off lid. This allows contamination of the inside of the container to be prevented.

A particularly advantageous refinement of a preferred embodiment of the present invention can provide the device to comprise a wiper that is preferably arranged in the region of the opening, in particular between the opening and the liquid.

In this context, a preferred embodiment of the present invention can provide the wiper to be disc-shaped and to comprise at least one notch that connects the top and the bottom of the disc. The implant can be introduced into the device through the at least one notch. It is particularly advantageous to have radial notches formed in the wiper. This enables the entire external circumference of the implants to be wiped off after coating is complete and thus to remove excess quantities of the solution or suspension from the coated implant surface. Moreover, it enables to effectively prevent the release of droplets of the liquid that might arise while the implant is pulled out of the liquid. Contamination during the surgery is thus largely prevented.

Moreover, a preferred embodiment of the present invention can provide the wiper to be shaped like an envelope of cone or a hemispherical surface, whereby the tip of the cone or the hemisphere is oriented towards the liquid and the envelope of cone or the hemisphere preferably contain at least one notch that connects the top and the bottom of the wiper.

A preferred embodiment of the present invention can also provide a transfer means to be arranged above the liquid that can be used to transfer a second liquid to the medical implant, whereby the second liquid is contained in the transfer means.

In this context, a preferred embodiment of the present invention can provide the transfer means to comprise pores and the pores of the transfer means to contain the second liquid, preferably in the form of a solution and/or suspension, whereby the second liquid preferably contains a second pharmaceutically active substance.

A refinement of a preferred embodiment of the present invention provides the transfer means to comprise at least one roller, at least one rotatable sphere and/or at least one sponge that can be used to transfer the second liquid to the medical implant surface to be coated. This allows the quantity of the second liquid to be used to be reduced and inadvertent mixing of major quantities of the second liquid with the (first) liquid to be prevented.

According to a particularly preferred refinement, a preferred embodiment of the present invention can provide the pharmaceutically active substance, and preferably the second pharmaceutically active substance as well, to contain antibiotics and/or organic antiseptic agents in a manner such that the coating to be generated contains a pharmaceutically active dose.

Moreover, a preferred embodiment of the present invention can provide the device to comprise a vacuum connection that can be connected to a vacuum source and is preferably arranged between the wiper and the liquid. This can ensure, in addition, through the aspiration of droplets of the liquid and, if applicable, remnants of powder that no contamination of the operating theatre through pharmaceutical agents occurs.

A preferred embodiment of the present invention can also provide for the wiper to be made of a biocompatible elastomer, thermoplastic material and/or a metal foil or composites that are manufactured from metal-elastomer combinations or metal-plastic combinations.

Moreover, a preferred embodiment of the present invention can provide the wiper as a ring that contains bristles that are arranged such as to be radial with respect to the centre of the container. The bristles can be made of plastic material, whereby the mechanical stability and anchoring of the bristles are sufficiently strong for the bristles to neither break off nor become detached.

According to a refinement, a preferred embodiment of the present invention provides the wiper in the form of rotatable or non-rotatable rollers and/or spheres that are connected to the container through elastic connecting means. The structure allows excess liquid, and excess powder if applicable, to be wiped off particularly easily.

According to a preferred embodiment of the present invention, the device can be pre-filled with a powder, a solution and/or a suspension of an agent such that the OR staff simply needs to open the device and can then proceed with the coating of the implant instantaneously. In this context, it is advantageous that the time expenditure for the coating is in the range of but a few seconds and valuable OR time can thus be saved.

Alternatively, it is feasible to provide a non-pre-filled device with one or more pharmaceutical agents right in the OR theatre through injection of a solution or suspension of an agent and/or filling it with a powder. In the case of the antibiotic coating, this enables suitable selection of an antibiotic or combination of antibiotics based on the existing resistance status and thus ensures that the coating matches the antibiotic sensitivity pattern.

It is also feasible to fill non-pre-filled devices with suitable solutions or suspensions of active substances in the respective hospital pharmacy prior to surgery such that coating can be carried out during the surgery without any time delay.

Examples of pharmaceutically active substances that can be used include antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

According to a preferred embodiment of the present invention, aqueous solutions of an antibiotic, preferably an aqueous gentamicin sulfate solution with a gentamicin sulfate content of 10.0 to 88.0% by weight can be provided as liquids, whereby a gentamicin sulfate solution with a gentamicin sulfate content of 75.0 to 80.0% by weight is particularly preferred. The gentamicin sulfate solution has an oily-viscous consistency and adheres very well to metal surfaces. Moreover, common pharmaceutical stabilisers may also be present in the gentamicin sulfate solutions.

The scope of a preferred embodiment of the present invention also includes the use of other aminoglycoside antibiotic solutions such as aqueous solutions of tobramycin sulfate, amikacin sulfate, netilmicin sulfate, and sisomycin sulfate. It is also feasible to use aqueous solutions of vancomycin, dalbavancin, ramoplanin, daptomicin, moxifloxacin, clindamycin, and/or lincomycin. The use of combinations of solutions of various antibiotics is also included in the scope of the invention. Examples include two-antibiotic combinations of gentamicin sulfate and vancomycin hydrochloride, the two-antibiotic combination of daptomycin and gentamicin sulfate, and the two-antibiotic combination of gentamicin sulfate and clindamycin as well as the three-antibiotic combination of gentamicin sulfate and vancomycin hydrochloride and clindamycin hydrochloride. Moreover, it is feasible to use antiseptic agent solutions in place of antibiotic solutions. Examples include solutions of chlorohexidine gluconate, octenidine dihydrochloride or polyhexanide.

The scope of a preferred embodiment of the present invention also includes the use of solutions of antibiotics and antiseptic agents that contain, as solvents, organic solvents or combinations of organic solvents or combinations of organic solvents and water.

This allows, for example, poorly water-soluble antibiotic salts, such as laurates, myristates, palmitates, and stearates, to be used as well. Moreover, poorly water-soluble antibiotics or antibiotic salts in the form of aqueous suspensions can also be used.

Preferably, the powder that is used, if applicable, contains a bone growth-promoting substance. The bone growth-promoting substance can, for example be selected from the group consisting of β-tricalcium phosphate, α-tricalcium phosphate, amorphous calcium phosphate, tetracalcium phosphate, octacalcium phosphate, hydroxylapatite, fluoroapatite, calcium sulfate hemihydrate, calcium sulfate dihydrate, anhydrous calcium sulfate, powdered antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof. The powder can also contain complexing agents or salts that form poorly water-soluble complexes or salts with the pharmaceutical agents that are transferred from the wiper to the implant surface. The powder can thus contain, for example, teicoplanin that forms poorly water-soluble complexes with gentamicin or other cationic antibiotics. It is also feasible, for example, that the powder contains N-methylglucammonium salts of fatty acids or of alkyl sulfates, which can form poorly water-soluble fatty acid salts or alkyl sulfates of the antibiotics upon exposure to aqueous solutions of cationic antibiotics owing to a reciprocal salt exchange. This means enables the application of poorly water-soluble complexes or salts of pharmaceutical agents, in particular of antibiotics, onto the implant surface.

It is particularly advantageous to use reactive inorganic powders, such as calcium phosphate made amorphous, tetracalcium phosphate and calcium sulfate hemihydrate, which harden in the presence of water. It is thus feasible to form stable coatings. Hardening within just a few seconds can be achieved, for example when calcium sulfate hemihydrate is used as the powder, through the addition of small amounts of calcium sulfate dihydrate as a nucleation agent and ammonium sulfate, sodium sulfate or potassium sulfate as accelerator to the calcium sulfate hemihydrate. Moreover, the use of β-tricalcium phosphate, α-tricalcium phosphate, and tetracalcium phosphate, which harden within just a few seconds upon exposure to the influence of aqueous acids, in particular of aqueous solutions of malic acid, tartaric acid, and citric acid, is also advantageous.

The scope of a preferred embodiment of the present invention further includes the provision of the device as a drug or medical product.

A combination of the device according to a preferred embodiment of the present invention and a medical implant could be offered as well. The combination is formed by the device and the implant, whereby the combination has a minimal service life of 0.1 seconds. The combination arises during the coating process.

A preferred embodiment of the present invention is based on the surprising finding that a liquid to be used to coat a medical implant can be applied to a medical implant even shortly before its use through simply immersing the implant into the liquid. The simple method and the device therefore ensure the usability in the OR as well.

For initial antibiotic protection, it is sufficient to have sufficiently high concentration(s) of antibiotic or antibiotics at the implant surfaces for a period of 24 to 72 hours. Therefore, sufficient temporary local antibiotic protection of the medical implant can be attained even upon local introduction of simple water-soluble antibiotics into a liquid.

Accordingly, rather than coating the medical implant much earlier during its manufacture, it can also be coated right before inserting it. This allows relatively short-acting coatings to be used as well. Moreover, even a layer that is still liquid can be used, which opens up new application fields and renders new active substances accessible.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Exemplary embodiments of the present invention shall be illustrated in the following on the basis of two schematic figures, though without limiting the scope of the present invention. In the figures.

DETAILED DESCRIPTION OF THE INVENTION

Figure 1:
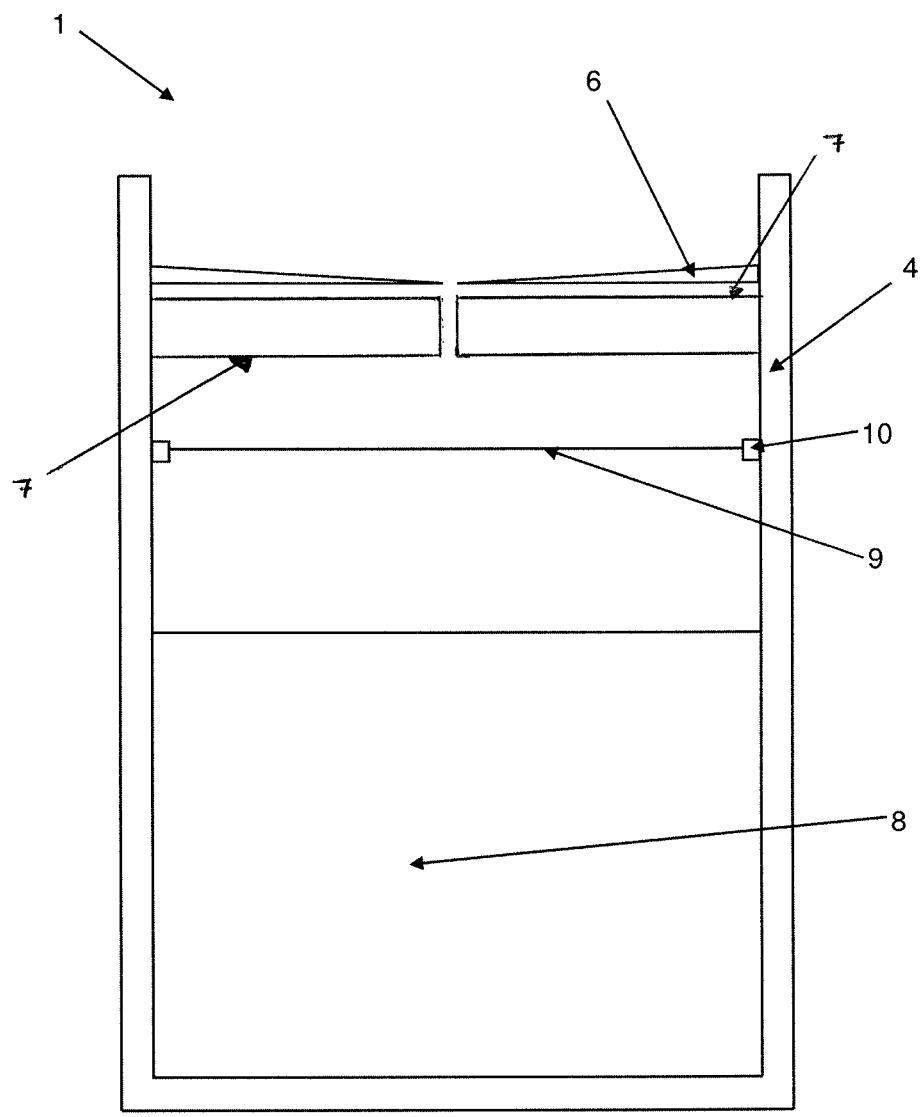
FIG. 1 is a schematic cross-sectional view of a device according to a preferred embodiment of the present invention.

Certain terminology is used in the following description for convenience only and is not limiting. The words "bottom" and "top" designate directions in the drawings to which reference is made. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIG. 1 shows a schematic cross-sectional view of a device 1 according to a preferred embodiment of the present invention. The device 1 preferably includes a container 4 in the form of a jar that is open on its top. Side walls of the container 4 are preferably cylindrical and of even thickness. A wiper 6 is preferably arranged on the inside of the container 4 in the region of the opening, shortly below the opening, and closes the opening.

The floor and side walls of the container 4 and the wiper 6 are manufactured from a hydrophobic material or coated with a hydrophobic layer. Originating from the centre of the wiper 6, the wiper 6 is slitted or notched in eight directions.

The eight slits/notches (not shown) do not reach all the way to the side walls of the container 4 and are meant to enable the introduction of a medical implant through the wiper 6. The wiper 6 thus has eight flexible segments that wipe off the medical implant while its is introduced or pulled out meaning that they sweep over the surface of the implant. This ensures that the wiper 6 essentially sweeps over the entire surface of the medical implant, in particular when it is being pulled out, and thus wipes it off.

A liquid 8 into which a medical implant can be immersed is contained inside the container 4. A membrane 9 is arranged above the liquid 8 and takes up the entire cross-section on the inside of the container 4. The liquid 8 is an aqueous solution containing antibiotics to be used for coating a medical implant.

The membrane 9 is supported through a bracketing ring 10 that is arranged on the inside of the container 4 below the wiper 6. The membrane 9 closes the container 4 in a sealed manner such that no contamination can penetrate from outside into the region below the membrane 9.

In one embodiment, a second liquid, preferably comprising at least one pharmaceutically active substance, is transferred through a transfer means 7 (located above the liquid 8) to the surface of the medical implant before immersing the medical implant into the liquid 8. For example, the medical implant may be swept over an elastically deformable transfer means 7, whereby the second liquid is transferred from the transfer means 7 to the medical implant surface to be coated while sweeping over the transfer means 7. In one embodiment, the transfer means 7 may also be porous, whereby the second liquid is stored in the pores of the transfer means 7 without the second liquid dripping into the liquid 8. The transfer means 7 may also or alternatively comprise at least one roller, at least one rotatable sphere and/or at least one sponge that can be used to transfer the second liquid to the medical implant surface to be coated.

The device 1 shown can be used to carry out a method according to a preferred embodiment of the present invention. A medical implant (not shown) is being pushed through the wiper 6. Subsequently, the medical implant punctures the membrane 9 which, until then, protected the liquid 8 situated below it from external influences. The medical implant is then immersed in the liquid 8. The medical implant is wetted through the liquid 8. Subsequently, the medical implant is pulled out of the liquid 8. Part of the liquid 8 remains adhering to the medical implant. Where the transfer means 7 having a second liquid is present, the medical implant is also swept over the transfer means 7 and coated with the second liquid.

Once the surface of the medical implant has been coated, the medical implant is pulled out of the container 4. The coated surface of the medical implant is pulled past the wiper 6 in the process. Excess liquid 8 is thus wiped off the surface of the medical implant. The medical implant pulled out of the container 4 is then coated, but does not drip any longer. This measure prevents the liquid 8 from contaminating the surroundings. The medical implant coated with the liquid 8 is then ready for use in a surgery.

The coating device 1 is manufactured from polypropylene, has a height of 25 cm and a diameter of 6 cm. The wiper 6 also consists of polypropylene. The membrane 9 is manufactured from aluminium compound foil. The bracketing ring 10 of the membrane 9 is manufactured from polypropylene and is pressed into a press-fit into the internal space of the container 4. Before its use, the container 4 can be closed in a germ-tight manner through an aluminium compound foil (not shown) that closes the opening of the container 4.

Figure 2:
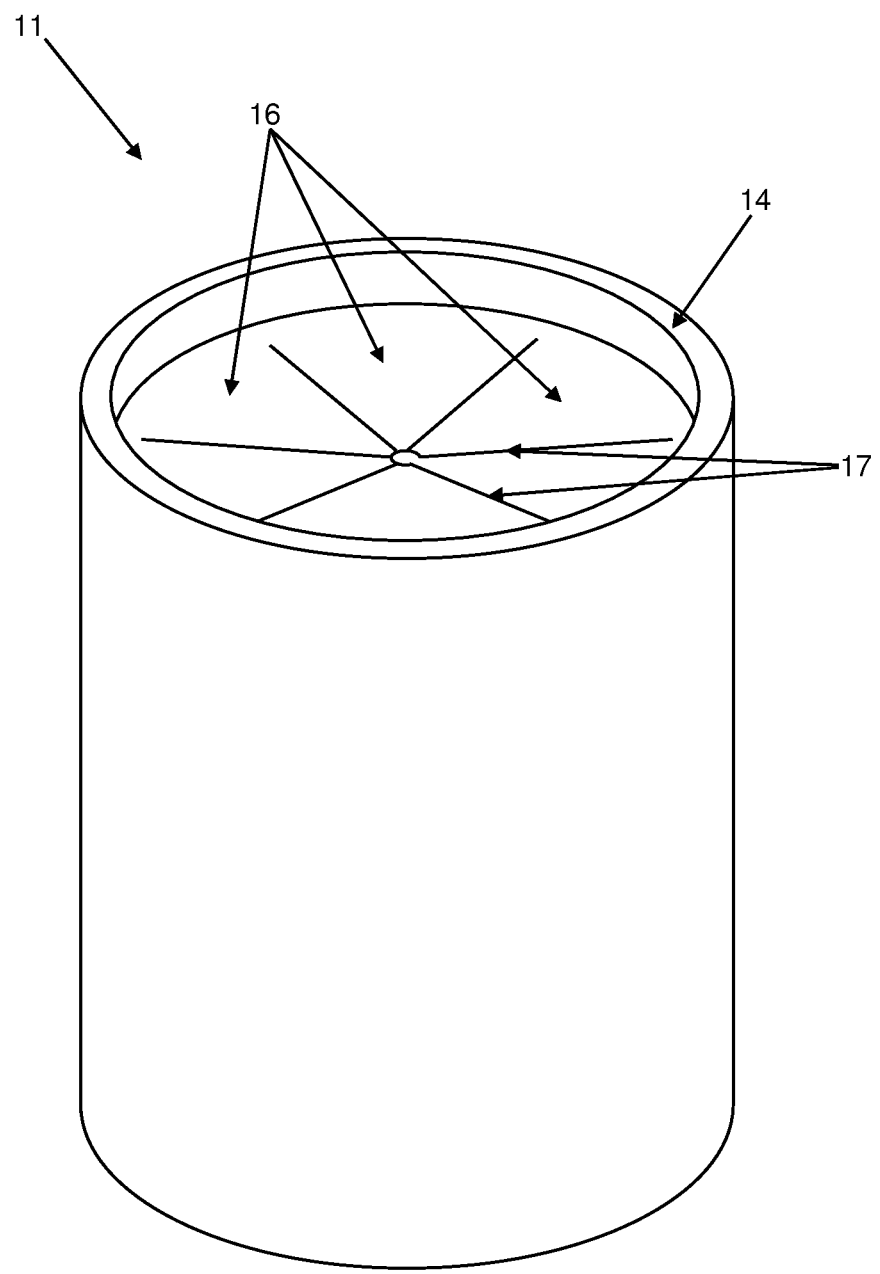
FIG. 2 is a schematic perspective view of a device according to a preferred embodiment of the present invention.

FIG. 2 shows a schematic perspective view of a second device 11 according to a preferred embodiment of the present invention for a method according to a preferred embodiment of the present invention. The device 11 preferably includes a container 14 and a wiper 16 that completely closes the container 14 on its top. The flexible wiper 16 preferably has six slits 17 or notches 17 that connect the top of the wiper 16 to the bottom of the wiper 16 facing the inside of the container 14 such that a medical implant (not shown) can be introduced into the inside of the container 14 through the wiper 16 along the slits 17 which are folded down in this situation.

A liquid (not shown) into which a medical implant can be immersed is contained on the inside of the container 14. The liquid contains a pharmaceutically active substance that is used to coat the medical implant as soon as the solvent of the liquid, in which the pharmaceutically active substance is dissolved, is evaporated.

According to a preferred embodiment of the present invention, common Zweymüller hip endoprostheses can be briefly inserted into the liquid-filled devices 1, 21 to the end of the stem and then be pulled out again instantaneously. The Zweymüller hip endoprostheses are thus furnished with a film of a liquid 8 at the surface of the stem. Once the liquid film dries up, the Zweymüller hip endoprostheses may show a white coating at the surface of the stem, in which the pharmaceutically active substance is contained. The hip endoprostheses are thus ready for use in a surgery.

After coating with the liquid 8, the medical implant can also be coated with a powder that is contained in a second container into which the medical implant can be inserted. The powder in the second container is preferably covered through a second membrane that is punctured and thus opened through the medical implant. The powder contains a bone growth-promoting substance such as calcium phosphate. The liquid film on the medical implant causes the powder to adhere well to the surface thereof. This results in a liquid-powder coating on the medical implant surface to be coated.

Examples of the production of liquids and powders for a method according to a preferred embodiment of the present invention and another example of a device according to a preferred embodiment of the present invention are illustrated in the following.

Example 1

Production of a Coating Solution Containing Gentamicin Sulfate

A total of 16.0 g gentamicin sulfate (Fujian Fukang Ltd.) were mixed with 4.0 ml pyrogen-free sterile water at room temperature. After stirring with a magnetic stirrer for 24 hours at room temperature, an oily-viscous yellowish solution had formed. A coating solution containing gentamicin sulfate as liquid for coating a medical implant was thus obtained.

Example 2

Production of a Coating Solution Containing the Two-Component Combination of Gentamicin Sulfate and Clindamycin Hydrochloride A total of 12.0 g gentamicin sulfate (Fujian Fukang Ltd.) were mixed with 4.0 g clindamycin hydrochloride (Sigma-Aldrich), and 4.0 ml pyrogen-free sterile water at room temperature. After stirring with a magnetic stirrer for 24 hours at room temperature, an oily-viscous yellowish solution had formed.

Example 3

Production of a Coating Solution Containing the Three-Component Combination of Gentamicin Sulfate, Clindamycin Hydrochloride, and Vancomycin Hydochloride A total of 4.0 g gentamicin sulfate (Fujian Fukang Ltd.), 4.0 g clindamycin hydrochloride (Sigma-Aldrich), and 4.0 g vancomycin hydrochloride (Sigma-Aldrich) were mixed with 8.0 ml pyrogen-free sterile water at room temperature. After stirring with a magnetic stirrer for 24 hours at room temperature, a viscous yellowish solution had formed.

Example 4

Production of a Coating Solution Containing Gentamicin Sulfate and Malic Acid

A total of 100 mg malic acid and 16.0 g gentamicin sulfate (Fujian Fukang Ltd.) were mixed with 4.0 ml pyrogen-free sterile water at room temperature. After stirring with a magnetic stirrer for 24 hours at room temperature, an oily-viscous yellowish solution had formed.

Example 5

Production of a Coating Solution Containing Gentamicin Sulfate and Citric Acid

A total of 100 mg citric acid and 16.0 g gentamicin sulfate (Fujian Fukang Ltd.) were mixed with 4.0 ml pyrogen-free sterile water at room temperature. After stirring with a magnetic stirrer for 24 hours at room temperature, an oily-viscous yellowish solution had formed.

Examples 6-10

Coating of Medical Implants

Conventional 10 ml plastic syringes were used to draw up 5 ml each of the coating solutions of examples 1-5 specified above. Then the filled plastic syringes were used to inject 4 ml of the corresponding agent solution into the container of a device according to the invention. Medical implants were coated with the solutions described in examples 1-5 through introducing them into the container and removing them from the container. Thus, medical implants were obtained that were coated with the antibiotics contained in the solutions used in each case.

Examples 11-15

Coating of Medical Implants with Antibiotic and Bone Growth-Stimulating Substances The procedure in examples 11-15 was consistent with the procedure used in examples 6-10, whereby the medical implants, after being pulled out of the container, were transferred into a second container and then were pulled out of the container. Closed through a second membrane, the second container was filled with a powder mixture of 150 g calcium sulfate hemihydrate (sieve fraction<64 μm), 15.0 g calcium sulfate dihydrate (sieve fraction<64 μm), and 1.5 g ammonium sulfate (sieve fraction<64 μm).

Examples 16-20

Coating of Medical Implants with Antibiotic and Other Bone Growth-Stimulating Substances The procedure in examples 16-20 was consistent with the procedure used in examples 6-10, whereby the medical implants, after being pulled out of the container, were transferred into a second container and then were pulled out of the container. The second container was filled with a powder mixture of 100 g calcium sulfate hemihydrate (sieve fraction<64 μm), 50.0 g calcium carbonate (sieve fraction<64 μm), 15.0 g calcium sulfate dihydrate (sieve fraction<64 μm), and 1.5 g ammonium sulfate.

Examples 21-25

Coating of Medical Implants with Antibiotic and Other Bone Growth-Stimulating Substances The procedure in examples 21-25 was consistent with the procedure used in examples 6-10, whereby the medical implants, after being pulled out of the container, were transferred into a second container and then were pulled out of the container. The second container was filled with 150 g β-tricalcium phosphate (sieve fraction<64 μm).

Examples 26-30

Coating of Medical Implants with Antibiotic and Other Bone Growth-Stimulating Substances The procedure in examples 26-30 was consistent with the procedure used in examples 6-10, whereby the medical implants, after being pulled out of the container, were transferred into a second container and then were pulled out. The second container was filled with 150 g α-tetracalcium phosphate (sieve fraction<64 μm).

In each of the examples 11-30, medical implants coated with the antibiotics used and the bone growth-stimulating substances used were obtained. The features of the present invention disclosed in the preceding description and in the claims, figures, and exemplary embodiments, can be essential for the implementation of the various embodiments of the invention both alone and in any combination.

It will be appreciated by those skilled in the art that changes could be made to the embodiments described above without departing from the broad inventive concept thereof.

It is understood, therefore, that this invention is not limited to the particular embodiments disclosed, but it is intended to cover modifications within the spirit and scope of the present invention as defined by the appended claims.

We claim:

1. A device (1, 11) for coating at least regions of a medical implant through a method comprising, introducing at least a portion of a medical implant through an opening in a container; immersing a surface of a medical implant into a liquid in the container, the liquid having at least one pharmaceutically active substance, whereby the liquid is transferred to the surface of the medical implant due to the immersing; and pulling the surface of the medical implant out of the liquid, whereby part of the liquid remains adhering to the surface of the medical implant, wherein at least a portion of the medical implant is introduced into the container, in which the liquid is situated, before immersing the surface of the medical implant into the liquid, and at least a portion of the medical implant is pulled out of the container after transfer of the liquid to the medical implant, and wherein part of the transferred liquid is wiped off upon pulling the medical implant out of the container at a wiper, wherein the device (1, 11) comprises:

the container (4, 14) including the liquid (8) having at least one pharmaceutically active substance, a membrane arranged above the liquid and sealing the liquid within the container (4, 14), a transfer means arranged above the membrane and storing a second liquid having at least one other pharmaceutically active substance, the wiper (6, 16) also being arranged above the membrane, and the opening of the container (4, 14) allowing for introducing and removing the medical implant.

2. The device (1, 11) according to claim 1, wherein the opening is closed by a pull-off lid.

3. The device (1, 11) according claim 1, wherein the wiper (6, 16) is disc-shaped and comprises at least one notch (17) that connects a top and a bottom of a disc (6).

4. The device (1, 11) according claim 1, wherein the wiper (6, 16) is shaped like an envelope of cone (16) or a hemisphere, whereby a tip of the cone or the hemisphere is oriented toward the liquid (8) and the envelope of cone (16) or the hemisphere preferably contains at least one notch (17) that connects a top and a bottom of the wiper (6, 16).

5. The device (1, 11) according to claim 1, wherein the pharmaceutically active substance contains antibiotics or organic antiseptic agents in a pharmaceutically active dose.

6. A device (1, 11) for coating at least regions of a medical implant through a method comprising, introducing at least a portion of a medical implant through an opening in a container; immersing a surface of a medical implant into a liquid in the container, the liquid having at least one pharmaceutically active substance, whereby the liquid is transferred to the surface of the medical implant due to the immersing; and pulling the surface of the medical implant out of the liquid, whereby part of the liquid remains adhering to the surface of the medical implant, wherein at least a portion of the medical implant is introduced into the container, in which the liquid is situated, before immersing the surface of the medical implant into the liquid, and at least a portion of the medical implant is pulled out of the container after transfer of the liquid to the medical implant, and wherein part of the transferred liquid is wiped off upon pulling the medical implant out of the container at a wiper, wherein the device (1, 11) comprises:

the container (4, 14) that has the liquid (8) that contains at least one pharmaceutically active substance, and the container (4, 14) comprises the opening for introducing and pulling out the medical implant, wherein the device (1, 11) comprises the wiper (6, 16) that is arranged in the region of the opening between the opening and the liquid (8) and a vacuum connection connectable to a vacuum source and between the wiper (6, 16) and the liquid (8).

* * * * *